(12) United States Patent
Van Der Mark et al.

(10) Patent No.: US 6,718,195 B2
(45) Date of Patent: Apr. 6, 2004

(54) METHOD OF AND DEVICE FOR LOCALIZING A DEVIANT REGION IN A TURBID MEDIUM

(75) Inventors: Martinus Bernardus Van Der Mark, Eindhoven (NL); Gert Wim 'T Hooft, Eindhoven (NL); Arthur Johannes Hubertus Wachters, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 510 days.

(21) Appl. No.: 09/819,282

(22) Filed: Mar. 28, 2001

(65) Prior Publication Data

US 2001/0026848 A1 Oct. 4, 2001

(30) Foreign Application Priority Data

Mar. 31, 2000 (EP) ............................................. 00201164

(51) Int. Cl.⁷ ................................................. A61B 6/00
(52) U.S. Cl. ..................... 600/473; 600/476; 600/407; 356/432; 250/341.1
(58) Field of Search ................................ 600/473, 476, 600/407, 438, 458, 410, 310, 475, 477; 356/432, 433; 250/573, 341.1, 339.06, 330, 338.1, 358.1

(56) References Cited

U.S. PATENT DOCUMENTS

| | | | | |
|---|---|---|---|---|
| 5,719,398 A | | 2/1998 | Colak | ...................... 250/341.1 |
| 5,800,354 A | * | 9/1998 | Hofland et al. | .............. 600/410 |
| 6,064,073 A | * | 5/2000 | Hoogenraad | ................. 250/573 |
| 6,230,045 B1 | * | 5/2001 | Hoogenraad et al. | ........ 600/473 |
| 6,327,489 B1 | * | 12/2001 | Hoogenraad et al. | ........ 600/407 |
| 6,436,043 B2 | * | 8/2002 | Bonnefous | ................... 600/438 |
| 6,533,727 B1 | * | 3/2003 | Brock-Fisher | .............. 600/458 |

FOREIGN PATENT DOCUMENTS

WO  WO9903394  1/1999  ............ A61B/5/00

OTHER PUBLICATIONS

"Clinical Optical Tomography and NIR Spectroscopy for Breast Cancer Detecton", by Colak et al, IEEE Journal of Selected Topics in Quantum Electronics, vol. 5, No. 4, Jul./Aug. 1999, pp. 1143–1154.

\* cited by examiner

Primary Examiner—Henry Bennett
Assistant Examiner—Fadi H. Dahbour

(57) ABSTRACT

The invention relates to methods of localizing a deviant region in a turbid medium. The invention also relates to devices for carrying out such methods. The methods can possibly be used in optical mammography where a breast of a female body is examined using light. Said methods produce images in which any deviations, for example tumors, can be clearly recognized. This is achieved inter alia by providing markers (10) in an image (9) of the turbid medium.

13 Claims, 3 Drawing Sheets

METHOD OF AND DEVICE FOR LOCALIZING A DEVIANT REGION IN A TURBID MEDIUM

BACKGROUND OF THE INVENTION

The invention relates to a method of localizing a deviant region in a turbid medium that is represented by a set of volume elements, which method includes a first measuring step in which the turbid medium is irradiated by means of light comprising radiation of mainly a fist wavelength and in which intensities of a part of the light comprising radiation of mainly the first wavelength that is transported along a plurality of light paths through the turbid medium are measured, and an imaging step for reconstructing an image of the turbid medium from the measured intensities.

The invention also relates to a device for carrying out such a method.

In the context of the present application the term light is to be understood to mean electromagnetic radiation of a wavelength in the visible or infrared range between approximately 400 and 1400 nm. A turbid medium is to be understood to mean a substance consisting of a highly light dispersive material. More specifically, in the context of the present application the term turbid medium is to be understood to mean biological tissue. A deviant region is to be understood to mean a region in which the turbid medium deviates in any way or form from the turbid medium in the surrounding region. More specifically, in the context of the present application such an area is to be understood to mean a region comprising tumor tissue. The turbid medium is represented by a set of volume elements. Volume elements of this kind are also known as voxels. The size and shape of the volume elements may be the same for all volume elements. However, it is alternatively possible for the volume elements to have mutually different dimensions and shapes.

A method and a device of this kind are known from "Clinical Optical Tomography and NIR Spectroscopy for Breast Cancer Detection", S. B. Colak et al, IEEE Journal of Selected Tops in Quantum Electronics, Vol. 5, No. 4, July/August 1999. The known method and device are used for imaging the interior of biological tissues. The method and the device can be used inter alia in medical diagnostics for in vivo breast examinations for visual localization of any tumors present in the breast tissue of a human or animal female body. According to the known method a turbid medium is successively irradiated by light from various irradiation positions. Subsequently, the intensity of the light having been transported along different light paths through the turbid medium that extend from their irradiation position is measured in a number of measuring positions. The intensities measured are used for the reconstruction of an image of the turbid medium. A spatial distribution of the attenuation of the light through the tissue is reproduced in this image. Light is attenuated by tissue in that the tissue disperses and absorbs the light.

A possibly deviant region can be visually localized in the image if the attenuation of the light by the tissue in the deviant region deviates sufficiently from the attenuation of the light by the tissue in the surrounding region. A plurality of individual images can be formed by carrying out the known method repeatedly while using light of different wavelengths.

The known method and device have a drawback in that the images thus obtained are insufficiently clear so as to enable accurate visual localization of deviant regions.

SUMMARY OF THE INVENTION

It is an object of the invention to provide a method that yields an image of the turbid medium in which deviant regions can be accurately localized visually.

This object is achieved by a method of the kind set forth in the preamble which is characterized in that the method also includes at least a second measuring step in which the turbid medium is irradiated by means of light comprising radiation of mainly a second wavelength which is not equal to the first wavelength, and in which intensities of a part of the light comprising radiation of mainly the second wavelength that is transported along a plurality of light paths through the turbid medium are measured, the imaging step including the following steps: a first calculation step in which a value is assigned to at least a first parameter in dependence on the intensities measured for a volume element in the measuring steps, said first parameter representing a property of the turbid medium, a second calculation step in which a significance value is assigned to the volume element in dependence on the value of at least the first parameter, a display step for displaying the significance value of the corresponding volume element in the image of the turbid medium for each point in the image that corresponds to one of the volume elements.

The invention is based on the one hand on the insight that the combining of measured intensities derived from a plurality of measurements with light of different wavelengths can yield values for parameters representing properties of the tissue, which properties enable (separately or in combination), normal tissue to be distinguished from deviant tissue. The parameters thus obtained can represent inter alia components constituting the turbid medium. For example, it is possible for a parameter to represent a spatial distribution of a quantity of water through the turbid medium.

The invention is also based on the recognition of the fact that regions that are deemed to be deviant on the basis of the parameter values obtained can be marked in the image. The attention of a user, for example a radiologist, is thus drawn to the region in the image that is considered to be deviant.

The significance value can be represented in the image of the turbid medium, for example by utilizing colors. Distinct colors can thus be assigned to different significance values. Should the significance value vary continuously, alternatively smoothly varying colors can be added to the image. Known color scales, for example the rainbow scale, can be used for this purpose.

A version of the method in accordance with the invention is characterized in that it includes a third measuring step in which the turbid medium is irradiated by means of light comprising radiation of mainly a third wavelength that is not equal to the first wavelength or the second wavelength and in which intensities of a part of the light comprising radiation of mainly the third wavelength that is transported along a plurality of light paths through the turbid medium are measured, and that in the first calculation step a value is assigned to a second parameter in dependence on the intensities measured for a volume element in the measuring steps, said second parameter representing a property of the turbid medium that is not the same as that represented by the first parameter, and that in the second calculation step a significance value is assigned to the volume element in dependence on the value of the first parameter and on the value of the second parameter.

Each measuring step in this version produces a set of measured data. The values for two parameters are determined from the three sets of measured data obtained. When the wavelengths of the light are sufficiently far apart in the three measuring steps, the sets of measured data will not be correlated and, using known mathematical techniques, it will in all cases be possible to determine values for the mutually independent parameters from the sets of measured data.

A version of the method in accordance with the invention is characterized in that the first wavelength has a value of between 830 nm and 900 nm, that the second wavelength has a value of between 750 nm and 830 nm, and that the third wavelength has a value of between 655 nm and 750 nm. Light with the above-mentioned wave lengths can easily be generated by state of the art semi-conductor lasers.

When the wavelengths of the light used in the three measuring steps lie in the above ranges, the spatial distribution of inter alia hemoglobin (Hb) and oxyhemoglobin (HbO$_2$) through the tissue can be suitably approximated. This is because the attenuation of the light due to dispersion and absorption by biological tissue is low in these regions and because for hemoglobin (Hb) the attenuation of the light as a function of the wavelength of the light deviates from that for oxyhemoglobin (HbO$_2$).

A particularly attractive result is obtained when the first wavelength has a value of approximately 867 nm while the second wavelength has a value of approximately 780 nm and the third wavelength has a value of approximately 715 nm or, as an alternative, a value of approximately 682 nm.

If an accurate determination of the ratio of fat to water in the tissue is desirable, a fourth measuring step may be added in which the light used contains radiation of a wavelength of between 1040 and 1070 nm or, as an alternative, of between 750 nm and 770 nm. A more accurate determination of the fat to water ratio also enables a more accurate determination of the spatial distribution of hemoglobin (Hb) and oxyhemoglobin (HbO$_2$) through the tissue.

An advantageous version of the method in accordance with the invention is characterized in that the first parameter represents a quantity of blood in a volume in the turbid medium that corresponds to one of the volume elements, and that the second parameter represents a deoxygenation ratio of blood in a volume in the turbid medium that corresponds to one of the volume elements.

In the context of the present invention a quantity of blood is to be understood to mean the sum of the quantities of hemoglobin (Hb) and oxyhemoglobin (HbO$_2$), while the deoxygenation ratio of blood is to be understood to mean the ratio (Hb)/(Hb+HbO$_2$).

Clinical tests performed by applicant have demonstrated that tumor tissue contains an increased quantity of blood per unit of volume and that, moreover, the deoxygenation ratio of the blood in tumor tissue is high in comparison with that in normal tissue. Furthermore, the quantity of blood and the deoxygenation ratio increase as a tumor is more malignant. Therefore, the quantity of blood in a volume and the deoxygenation ratio are suitable parameters, both individually and in combination, for use in the method in accordance with the invention for the to localization of a tumor, if any, in the image.

A further advantageous version of the method in accordance with the invention is characterized in that the parameters define a parameter space, that in the second calculation step the volume elements are assigned a position in the parameter space in dependence on the values assigned to the parameters for the relevant volume element, and that the significance value assigned to a volume element is determined by the position of the volume element in the parameter space.

Depending on the number of parameters, such a parameter space may be one-dimensional (a line), two-dimensional (a plane), three-dimensional (a space or volume) or even more dimensional. The parameters then represent the system of co-ordinates of the parameter space. A volume element is assigned a position in said parameter space, the co-ordinates of said position being formed by the values associated with the parameters. For example, in a two-dimensional parameter space a volume element with a value X assigned to a first parameter and a value Y assigned to a second parameter will be assigned a position in the parameter space that has the co-ordinate (X,Y).

Such a parameter space may be virtually present in the device that is used to carry out the method. Moreover, the parameter space can also be shown to the user. For example, a two-dimensional parameter space can be displayed on a display screen.

A version of the method in accordance with the invention is characterized in that the parameter space is subdivided into at least a first sub-space and a second sub-space, that the volume elements are assigned a first significance value when they occupy a position in the first sub-space and that the volume elements are assigned a second significance value when they occupy a position in the second sub-space.

The parameter space can be subdivided into sub-spaces by hand as well as automatically. For example, a user can manually indicate a sub-space in a two-dimensional parameter space displayed on a display screen; the volume elements that are situated in said sub-space are then assigned a significance value that is indicative of a deviant region. The user can choose this sub-space, for example, by comparing the distribution of the positions of the volume elements across the parameter space with a reference distribution. During an examination of the breast tissue of a human female body the distribution of the positions of the volume elements across the parameter space that is found for one breast can thus be compared with that found for the other breast.

The automatic subdivision of the parameter space into sub-spaces can be performed, for example, by subdividing the parameter space into predetermined sub-spaces. Performing a number of reference measurements, thus enables determination in advance as to how the sub-spaces should be distributed across the parameter space and as to what significance value should be assigned to the volume elements in each of the sub-spaces. Alternatively, it is possible to realize the automatic subdivision by means of known segmentation techniques. In that case, for example, the percentage of the number of volume elements that should be situated in a first sub-space and the percentage of the number of volume elements that should be situated in a second sub-space can be indicated in advance.

Even though the parameter space is subdivided into two sub-spaces in the above description, it will be evident to those skilled in the art that a subdivision into a larger number of sub-spaces is also possible. For each sub-space a distinct significance value can then be assigned to the volume elements situated within each of the sub-spaces. It is also possible to assign for a plurality of sub-spaces the same significance value to the volume elements that are situated in such sub-spaces.

A version of the method in accordance with the invention is characterized in that the significance value is determined at least by the distance between the position assigned to the volume element and a selected position in the parameter space.

For example, the distance between two points in conformity with Euclid's geometric principles can be used as a measure of the distance. For example, the distance between two points $P_1(x_1, y_1)$ and $P_2(x_2, y_2)$ that are situated in a two-dimensional parameter space, where $x_1$ represents a first value and $x_2$ represents a second value for the parameter X and where $y_1$ represents a first value and $y_2$ represents a second value for the parameter Y, is equal to $\sqrt{(x_1-x_2)^2+(y_1-y_2)^2}$.

For example, the center of gravity of the distribution of the positions of the volume elements in the parameter space can be selected as the selected position. The significance value assigned to a volume element may be a continuously varying value in dependence on the distance. However, the distance may also be subdivided into a number of discrete steps, a significance value being associated with each step.

A further version of the method in accordance with the invention is characterized in that the significance value is determined inter alia by the situation of the position assigned to the volume element relative to the selected position.

In addition to the distance from the selected position, the situation of the position assigned to the volume element relative to the selected position is also decisive in respect of the significance value to be assigned to the volume element. For example, a volume element with high parameter values may be assigned a significance value other than the significance value assigned to a volume element that is situated at the same distance from the selected point but has low parameter values.

The object of the invention is also achieved by means of a method of the kind set forth in the preamble which is characterized in that the method also includes at least a second measuring step in which the turbid medium is irradiated by light comprising radiation of mainly a second wavelength which is not equal to the first wavelength and where intensities of a part of the light comprising radiation of mainly the second wavelength, that is transported along a plurality of light paths through the turbid medium are measured, and that the imaging step includes the following steps: a first calculation step in which a value is assigned to at least a first parameter in dependence on the intensities measured in the measuring steps for a volume element, which first parameter represents a property of the turbid medium, and a reconstruction step for reconstructing an image of the turbid medium from at least the value assigned to the first parameter for the volume element.

The invention is based on the recognition of the fact that the combining of measured intensities obtained from a plurality of measurements with light of different wavelengths can yield values for parameters that represent tissue properties that enable, individually or in combination, normal tissue to be distinguished from deviant tissue. The parameters thus obtained may represent inter alia constituent components of the turbid medium.

The imaging of such parameters yields an image in which a deviant region can be localized more accurately than in an image of the attenuation of the light by the tissue. This is the case inter alia when the parameters represent constituent components of the turbid medium. For example, in an image of the spatial distribution of a deoxygenation ratio of blood, $(Hb)/(Hb+HbO_2)$, in female breast tissue a region with tumor tissue will be visually perceptible because, generally speaking, the deoxygenation ratio in tumor tissue is higher than that in normal tissue. Similarly, in an image of the quantity of blood, $(Hb+HbO_2)$, per unit of volume a region with tumor tissue will be visually perceptible, because the blood circulation in tumor tissue generally is greater than that in normal tissue.

An image can be reconstructed from the parameter values by application of reconstruction techniques that are also used for the reconstruction of an image of the attenuation of the light by tissue from the measured intensities. Examples of such reconstruction techniques are the 3-D Algebraic Reconstruction Technique according to Hoogenraad and the 3-D Conjugent Gradient Technique according to Wachters.

It is to be noted that the described method is suitable not only for the imaging of biological tissue with a view to detecting deviant regions, but also for the imaging of functional properties of biological tissue. For example, images can be formed of the blood circulation and of the oxygen content of the blood in the brain of infants.

It is a further object of the invention to provide a device for producing an image of the turbid medium in which deviant regions can be accurately localized visually.

This object is achieved by means of a device of the kind set forth in the opening paragraph which is characterized in that it also includes means for irradiating the turbid medium by means of light comprising radiation having of mainly a second wavelength which is not equal to the first wavelength, means for measuring intensities of a part of the light comprising radiation of mainly the second wavelength that is transported along a plurality of light paths through the turbid medium, and means for assigning, in dependence on the measured intensities for a volume element, a value to at least a first parameter which represents a property of the turbid medium, and means for assigning a significance value to the volume element in dependence on the value of at least the first parameter, and means for displaying the significance value of the corresponding volume element in the image of the turbid medium for each point in the image that corresponds to one of the volume elements.

This object is also achieved by means of a device of the kind set forth in the opening paragraph which is characterized in that it also includes means for irradiating the turbid medium by means of light comprising radiation of mainly a second wavelength which is not equal to the first wavelength, and also means for measuring intensities of a part of the light comprising radiation of mainly the second wavelength that is transported along a plurality of light paths through the turbid medium, and means for assigning, in dependence on the measured intensities for a volume element, a value to at least a first parameter which first represents a property of the turbid medium, and means for reconstructing the image of the turbid medium from at least the value assigned to the first parameter for the volume element.

The devices mentioned in the previous paragraphs are, for example, implemented in the form of an medical diagnostic workstation.

The invention further relates to a computer program for carrying out the methods according to the invention. This computer program may comprise instructions for carrying out all of the versions of the methods according to the invention or, alternatively, may comprise instructions for carrying out a sub-set of the versions of the methods. The instructions of this computer program are, for example, loaded into the memory of a medical diagnostic workstation and are subsequently executed by a processor in this workstation. According to a further object of the invention, the computer program is recorded on a record carrier, such as for example a CD-ROM disc or a magnetic tape. The instructions of the computer program are transferred from the record carrier into the memory of, for example, a medical diagnostic workstation. Alternatively, the instructions of the computer program are transferred from the record carrier into the memory of a PC or any other standard computer system. It is also possible to load the computer program into a memory through a network such as, for example, the "World-Wide Web".

BRIEF DESCRIPTION OF THE DRAWINGS

The above and other, more detailed aspects of the invention will be described in detail hereinafter, by way of example, with reference to the drawings. Therein.

DETAILED DESCRIPTION OF THE PREFERRED EMBODIMENT

Figure 1:
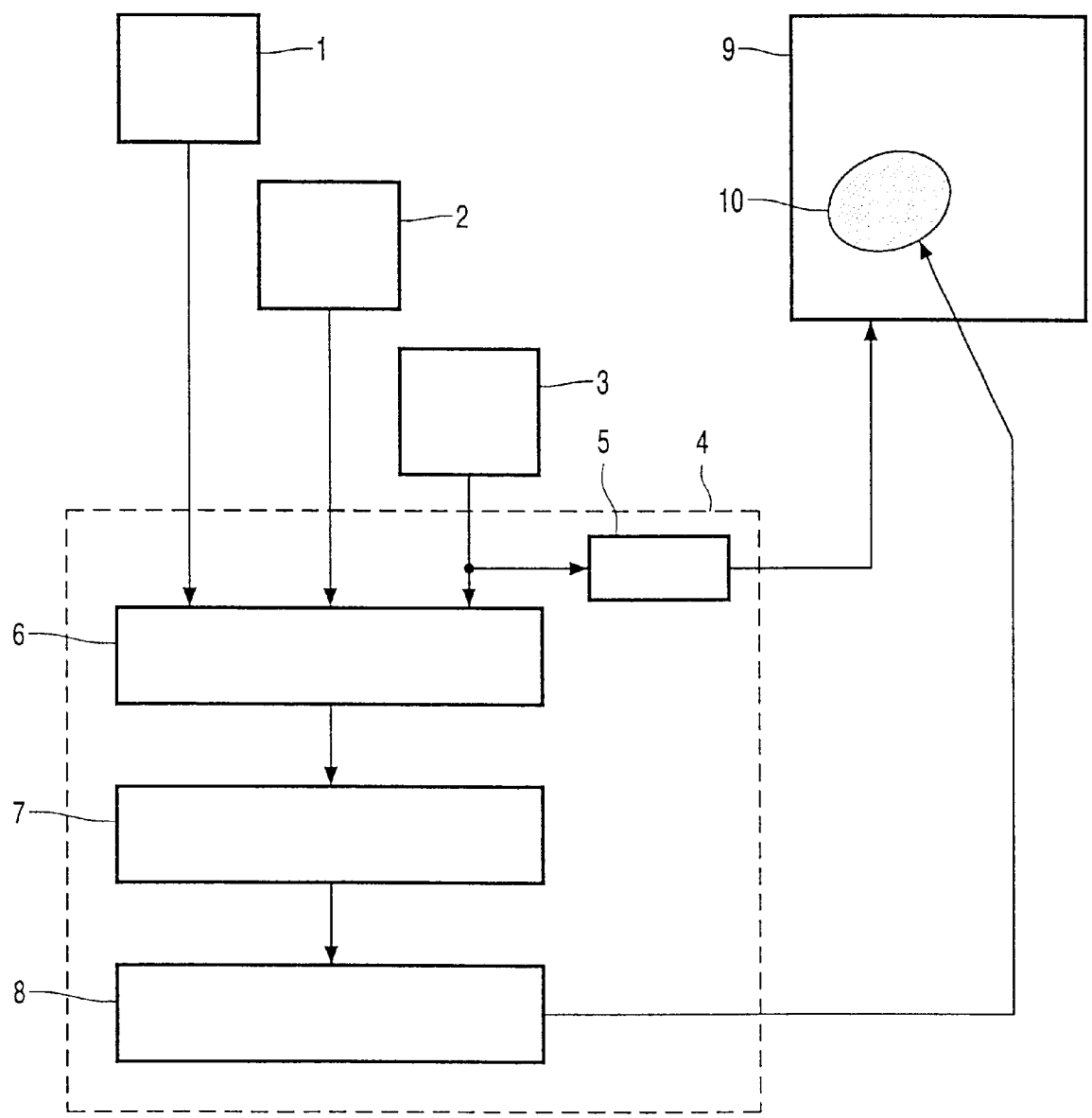
FIG. 1 illustrates diagrammatically a first method in accordance with the invention.

FIG. 1 shows diagrammatically a first method in accordance with the invention. During a first measuring step 1 the turbid medium is irradiated by means of light-comprising radiation of mainly a wavelength of 867 nm and the intensity of a part of the light that is transported along a plurality of light paths through the turbid medium is measured. Such a measuring step is described in greater detail in European patent application 98925884.3 (PHN 16.442). Subsequently, a second, similar measuring step 2 is performed by means of light comprising radiation of mainly a wavelength of 780 nm, followed by a third measuring step 3 while using light comprising radiation of mainly a wavelength of 715 nm.

Using a reconstruction algorithm 5 in an imaging step 4, an image 9 of the turbid medium is reconstructed from the intensities measured in the third measuring step 3. Even though an image is reconstructed from the intensities measured in the third measuring step 3 in the present example, the intensities measured in the first measuring step 1 or the second measuring step 2 can also be used for this purpose.

In a first calculation step 6 for each volume element two parameters are determined from the three sets of intensities measured in the three measuring steps. These parameters, representing local characteristics of the tissue examined, are the quantity of blood in a volume and the deoxygenation ratio of the blood in a volume in the present example. In this context a quantity of blood in a volume is to be understood to mean the sum of the hemoglobin and the oxyhemoglobin ($Hb+HbO_2$) present in the volume. The term deoxygenation ratio of the blood in a volume is to be understood to mean herein the ratio of the hemoglobin present in the volume to the quantity of blood present in a volume ($Hb$)/($Hb+HbO_2$). These parameters are particularly suitable for the localization of tumor tissue in breast tissue, because tumors are generally characterized by a higher blood circulation and a higher oxygen consumption, leading to an increase of both parameters.

In a second calculation step 7 the volume elements are mapped in a two-dimensional parameter space 20, an example of which is shown in FIG. 2. This parameter space 20 is defined by the two parameters determined in the first calculation step 6. In the present example the quantity of blood in a volume is represented by the horizontal X axis 22 and the deoxygenation ratio of the blood in a volume is represented by the vertical Y axis 21. A volume element in this parameter space is assigned a position 23 which is dependent on the values of the two parameters for the relevant volume element. Thus, a volume element having a value $X_1$ for the quantity of blood in a volume and a value $Y_1$ for the deoxygenation ratio of the blood in a volume will be assigned a position having the co-ordinate ($X_1, Y_1$) in the parameter space.

Figure 2A:
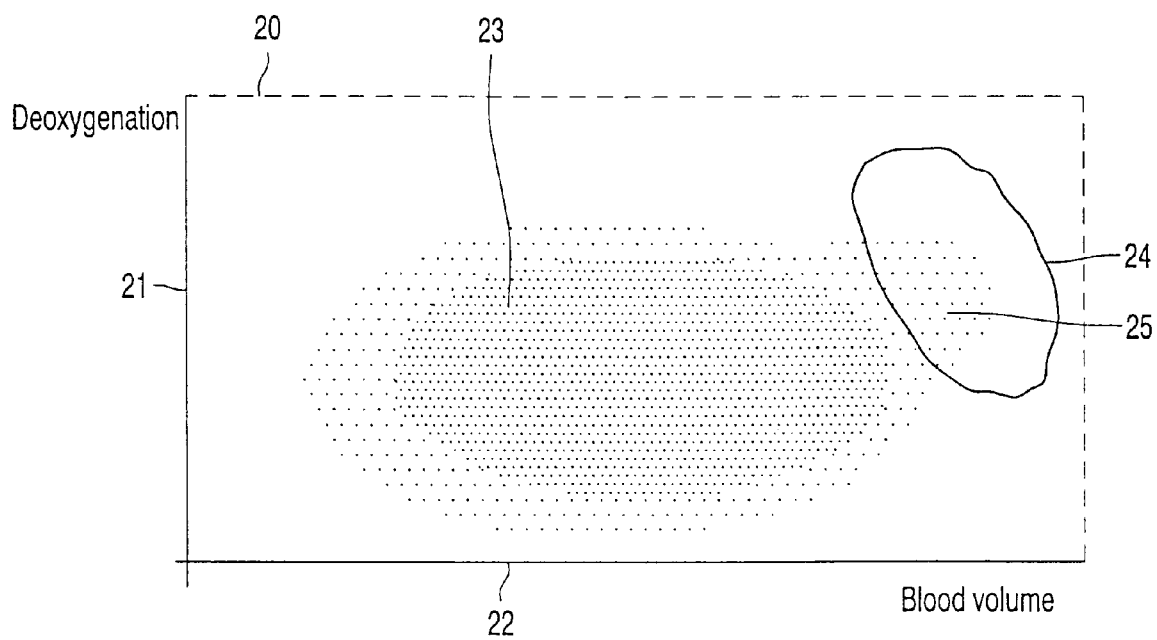
FIG. 2 shows an example of a two-dimensional parameter space.

Subsequently, each volume element is assigned a significance value which is dependent on the position 23 of the volume element in the parameter space 20. In the present example a volume element is assigned a significance value "1" if it is deemed to be situated in a deviant region and a significance value "0" if it is deemed to be situated in a region outside the deviant region. FIG. 2A shows a sub-region 24 that contains high values for both parameters and is indicative of tumor tissue as discussed above. Volume elements having a position 25 in the sub-region 24 are assigned a significance value "1". The other volume elements are assigned a significance value "0". Even though only two distinct significance values are used in the present example, a plurality of discrete significance values can be used when the parameter space is subdivided into a plurality of sub-regions. It is also possible to use a continuously varying significance value. The significance value then represents, for example a probability value.

Subsequently, the significance values assigned to the volume elements in the image 9 of the turbid medium are reproduced in the display step 8. A dot in the image 9 that corresponds to a volume element is assigned, for example, a red color if the significance value assigned to the relevant volume element is "1" and a grey color if the significance value assigned to the relevant volume element is "0". Thus, an image 9 is formed of the turbid medium which contains grey values and a region 10 with red values. The region 10 corresponds to a deviant region in the turbid medium. It will be evident to those skilled in the art that other colors and other methods can also be used to mark a region in an image.

FIG. 2 shows an example of a two-dimensional parameter space 20. The parameter space 20 is defined by two parameters. A first parameter is represented by the horizontal X axis 22 and a second parameter by the vertical Y axis 21. A volume element in this parameter space is assigned a position 23 which is dependent on the values of the two parameters for the relevant volume element. Thus, a volume element having a value $X_1$ for the first parameter and a value $Y_1$ for the second parameter will be assigned a position in the parameter space that has the co-ordinate ($X_1, Y_1$).

In FIG. 2A the parameter space is subdivided into two sub-regions by manual formation of a sub-region 24. The volume elements 25 that are situated in the sub-region 24 were assigned a significance value that deviates from that assigned to the volume elements situated outside the sub-region 24. During the imaging of breast tissue the position and the shape of the sub-region 24 can be selected by comparing a parameter space obtained from measurements performed on one breast with a parameter space obtained from measurements performed on the other breast.

Figure 2B:
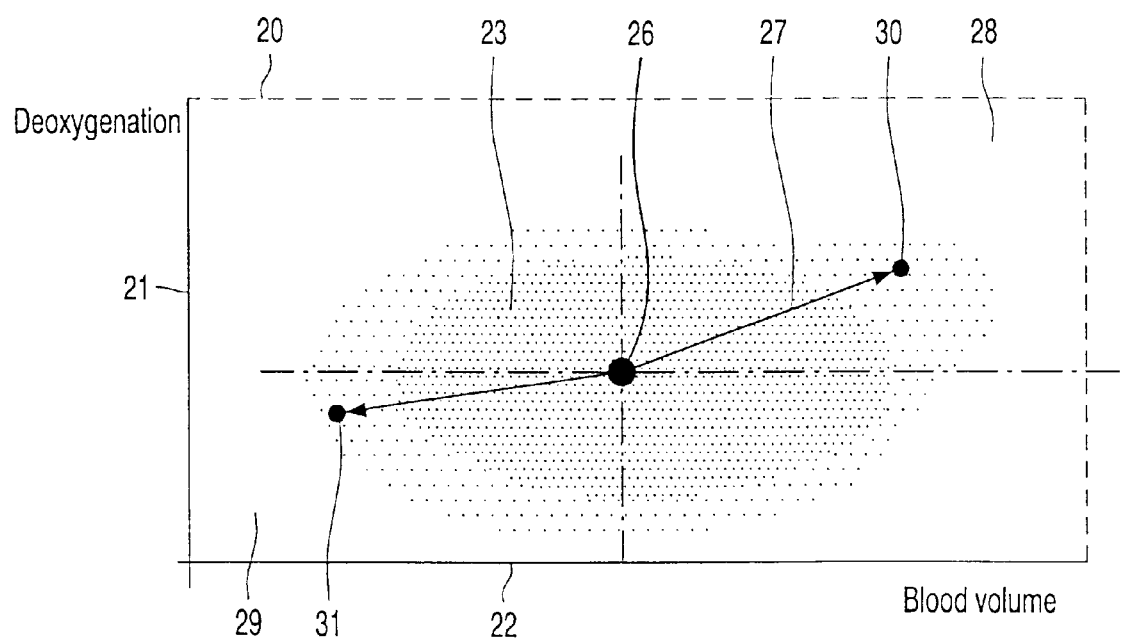

FIG. 2B shows an alternative method of assigning significance values to the volume elements. A volume element is now assigned a significance value that is dependent on the distance 27 between the position 30 of the volume element in the parameter space 20 and a selected position 26. In the present example the selected position 26 is the geometrical center of gravity of the distribution of the positions of the volume elements in the parameter space 20. The significance value to be assigned may be a continuous function of the distance 27. The distance 27 may alternatively be subdivided into a number of discrete steps, each step having an associated significance value.

Even though the position 30 of a first volume element and the position 31 of a second volume element are situated at the same distance from the selected position 26, a different significance value can still be assigned to the two volume elements as an alternative. The orientation of the positions of the volume elements relative to the selected point 26 is then also important. For example, the volume element with the position 30 that is situated in the upper right-hand quadrant 28 of the parameter space 20 will be assigned a significance value which differs from that assigned to the volume element with the position 31 that is situated in the lower left-hand quadrant 29 of the parameter space 20. This makes sense, for example, if the quantity of blood in a volume and the deoxygenation ratio of the blood in a volume are chosen as the parameters. As has already been described, an increased value of both parameters is indicative of tumor tissue. This is the case for the volume elements situated in the upper right-hand quadrant 28; therefore, these volume elements should be assigned a high significance value. However, a reduced value of one or both parameters has no significance. Therefore, the volume elements that are situated in one of the other three quadrants should not be assigned a high significance value on the basis of these two parameters.

Figure 3:
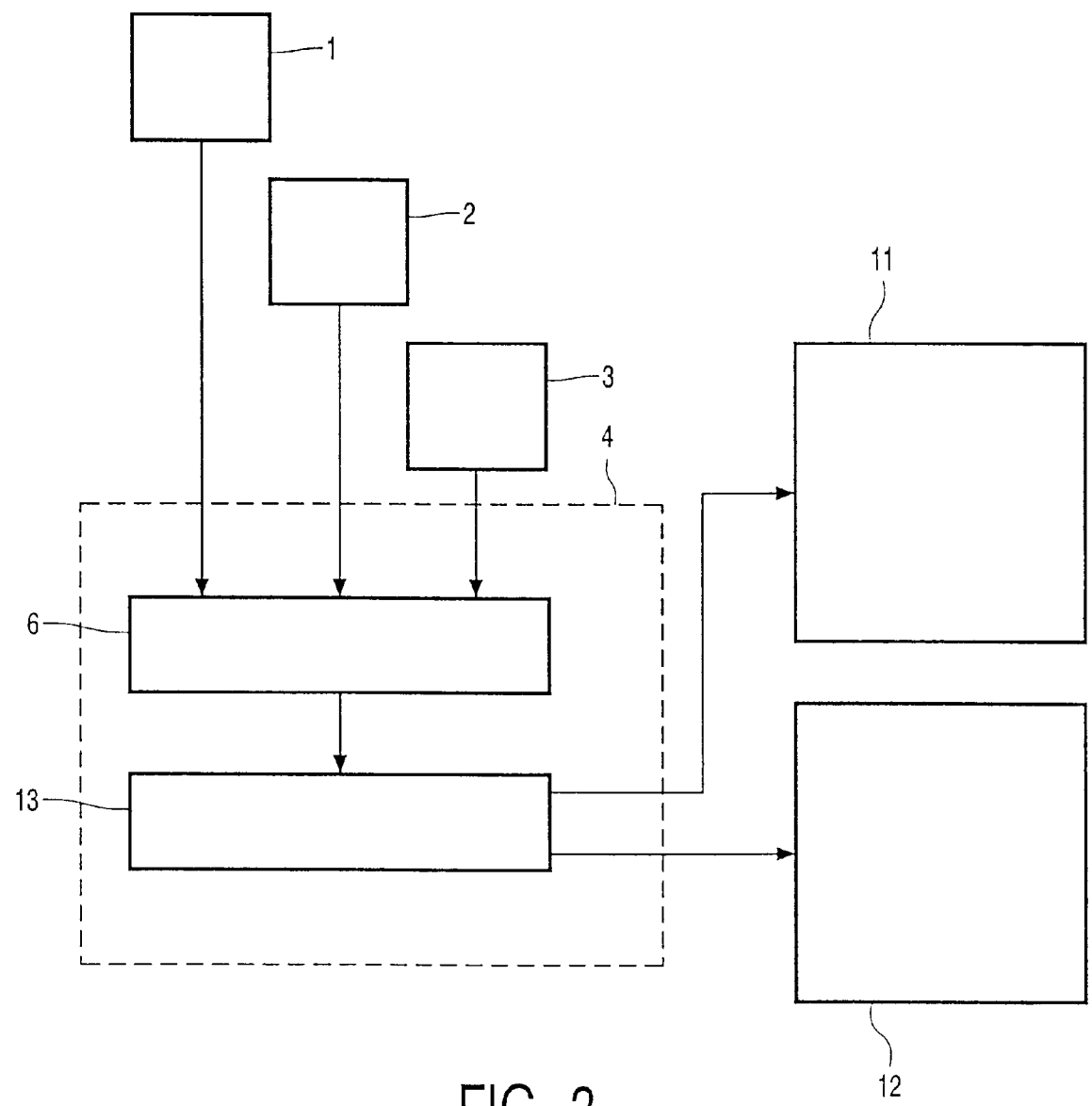
FIG. 3 illustrates diagrammatically a second method in accordance with the invention.

FIG. 3 illustrates diagrammatically a second method in accordance with the invention. During a first measuring step 1 the turbid medium is irradiated by means of light-comprising radiation of mainly a wavelength of 867 nm and the intensity of a part of the light that is transported along a plurality of light paths through the turbid medium is measured. Subsequently, a second, similar measuring step 2 is performed while using light comprising radiation of mainly a wavelength of 780 nm and also a third measuring step 3 that utilizes light comprising radiation of mainly a wavelength of 715 nm.

In a first calculation step 6 for each volume element two parameters are determined from the three sets of intensities measured in the three measuring steps. Subsequently, in a reconstruction step 13 the value of the first parameter for a volume element is imaged in an image 11 and the value of the second parameter is imaged in an image 12. A point in the image 11 and a point in the image 12 then correspond to the volume element. This yields an image of the spatial distribution of a parameter across the turbid medium.

When the parameters are suitably chosen, a deviant region will be clearly visible in the images. For example, when the quantity of blood in a volume is imaged in the image 11 and the deoxygenation ratio of the blood in a volume is imaged in the image 12, a region with tumor tissue that is present in the breast tissue will be visible because both parameters have an increased value in the tumor tissue.

The two parameters are separately imaged in the present example. However, it is also possible to image only one of the two parameters. It is furthermore possible to image more than two parameters separately if more than two parameters are determined in the first calculation step 6. Furthermore, the images of a plurality of parameters can be combined so as to form one common image.

What is claimed is:

1. A method of localizing a deviant region in a turbid medium that is represented by a set of volume elements, which method includes
   a first measuring step (1) in which the turbid medium is irradiated by means of light comprising radiation of mainly a first wavelength and in which intensities of a part of the light comprising radiation of mainly the first wavelength that is transported along a plurality of light paths through the turbid medium are measured,
   and an imaging step (4) for reconstructing an image (9) of the turbid medium from the measured intensities,
   characterized in that
   the method also includes at least a second measuring step (2) in which the turbid medium is irradiated by means of light comprising radiation of mainly a second wavelength which is not equal to the first wavelength,
   and in which intensities of a part of the light comprising radiation of mainly the second wavelength that is transported along a plurality of light paths through the turbid medium are measured,
   and that the imaging step (4) includes the following steps:
   a first calculation step (6) in which a value is assigned to at least a first parameter in dependence on the intensities measured for a volume element in the measuring steps, said first parameter representing a property of the turbid medium,
   a second calculation step (7) in which a significance value is assigned to the volume element in dependence on the value of at least the first parameter,
   a display step (8) for displaying in the image of the turbid medium (9) for a point in the image that corresponds to one of the volume elements, the significance value (10) of the corresponding volume element.

2. A method as claimed in claim 1, characterized in that the method includes a third measuring step (3) in which the turbid medium is irradiated by means of light comprising radiation of mainly a third wavelength that is not equal to the first wavelength or the second wavelength,
   and in which intensities of a part of the light comprising radiation of mainly the third wavelength that is transported along a plurality of light paths through the turbid medium are measured,
   and that in the first calculation step (6) a value is assigned to a second parameter in dependence on the intensities measured for a volume element in the measuring steps, said second parameter representing a property of the turbid medium that is not the same as that represented by the first parameter,
   and that in the second calculation step (7) a significance value is assigned to the volume element in dependence on the value of the first parameter and on the value of the second parameter.

3. A method as claimed in claim 2, characterized in that the first wavelength has a value of between 830 nm and 900 nm, that the second wavelength has a value of between 750 nm and 830 nm, and that the third wavelength has a value of between 655 nm and 750 nm.

4. A method as claimed in claim 3, characterized in that the first parameter represents a quantity of blood in a volume in the turbid medium that corresponds to one of the volume elements,
   and that the second parameter represents a deoxygenation ratio of blood in a volume in the turbid medium that corresponds to one of the volume elements.

5. A method as claimed in claim 1, characterized in that the parameters define a parameter space (20), that in the second calculation step (7) the volume elements are assigned a position (23) in the parameter space (20) in dependence on the values assigned to the parameters for the relevant volume element, and that the significance value assigned to a volume element is determined by the position of the volume element in the parameter space.

6. A method as claimed in claim 5, characterized in that the parameter space (20) is subdivided into at least a first sub-space (24) and a second sub-space, that the volume elements are assigned a first significance value when they occupy a position in the first sub-space, and that the volume elements are assigned a second significance value when they occupy a position in the second sub-space.

7. A method as claimed in claim 5, characterized in that the significance value is determined at least by the distance between the position (23) assigned to the volume element and a selected position (26) in the parameter space.

8. A method as claimed in claim 7, characterized in that the significance value is determined inter alia by the situation of the position assigned to the volume element relative to the selected position.

9. A method of localizing a deviant region in a turbid medium that is represented by a set of volume elements, which method includes a first measuring step (1) in which the turbid medium is irradiated by means of light comprising radiation of mainly a first wavelength, and in which intensities of a part of the light comprising radiation of mainly the first wavelength that is transported along a plurality of light paths through the turbid medium are measured, and an imaging step (4) for reconstructing an image of the turbid medium, characterized in that the method also includes at least a second measuring step (2) in which the turbid medium is irradiated by means of light comprising radiation of mainly a second wavelength which is not equal to the first wavelength, and in which intensities of a part of the light comprising radiation of mainly the second wavelength that is transported along a plurality of light paths through the turbid medium are measured, and that the imaging step (4) includes the following steps:
a first calculation step (6) in which a value is assigned to at least a first parameter in dependence on the intensities measured for a volume element in the measuring steps, said first parameter representing a property of the turbid medium,
a reconstruction step (13) for reconstructing an image (11) of the turbid medium from at least the value assigned to the first parameter for the volume element.

10. Computer program comprising a set of instructions for carrying out the method according to claim 1 or 9.

11. Record carrier comprising the computer program according to claim 12.

12. A device for imaging a deviant region in a turbid medium which is represented by a set of volume elements, which device includes means for irradiating the turbid medium by means of light comprising radiation of mainly a first wavelength, means for measuring intensities of a part of the light comprising radiation of mainly the first wavelength that is transported along a plurality of light paths through the turbid medium, and means for reconstructing an image of the turbid medium from the measured intensities, characterized in that the device also includes means for irradiating the turbid medium by means of light comprising radiation of mainly a second wavelength which is not equal to the first wavelength, and also means for measuring intensities of a part of the light comprising radiation of mainly the second wavelength that is transported along a plurality of light paths through the turbid medium, and means for assigning, in dependence on the measured intensities for a volume element a value to at least a first parameter which represents a property of the turbid medium, and means for assigning a significance value to the volume element in dependence on the value of at least the first parameter, and means for displaying the significance value of the corresponding volume element in the image of the turbid medium for each point in the image that corresponds to one of the volume elements.

13. A device for imaging a deviant region in a turbid medium which is represented by a set of volume elements, which device includes means for irradiating the turbid medium by means of light comprising radiation of mainly a first wavelength, means for measuring intensities of a part of the light comprising radiation of mainly the first wavelength that is transported along a plurality of light paths through the turbid medium, and means for reconstructing an image of the turbid medium, characterized in that the device also includes means for irradiating the turbid medium by means of light comprising radiation of mainly the second wavelength that is not equal to the first wavelength, means for measuring intensities of a part of the light comprising radiation of mainly the second wavelength that is transported along a plurality of light paths through the turbid medium, means for assigning, in dependence on the measured intensities for a volume element, a value to at least a first parameter which represents a property of the turbid medium, and means for reconstructing the image of the turbid medium from at least the value assigned to the first parameter for the volume element.

* * * * *